US00PP15926P3

(12) United States Plant Patent
Schlueter

(10) Patent No.: US PP15,926 P3
(45) Date of Patent: Aug. 23, 2005

(54) *HIBISCUS ROSA-SINENSIS* PLANT NAMED 'SMILEY FACE'

(50) Latin Name: ***Hibiscus rosa-sinensis* L.**
Varietal Denomination: Smiley Face

(75) Inventor: Barry Schlueter, Houston, TX (US)

(73) Assignee: Hines Nurseries, Inc., Irvine, CA (US)

( * ) Notice: Subject to any disclaimer, the term of this patent is extended or adjusted under 35 U.S.C. 154(b) by 112 days.

(21) Appl. No.: 10/764,025

(22) Filed: Jan. 23, 2004

(65) Prior Publication Data

US 2005/0166294 P1 Jul. 28, 2005

(51) Int. Cl.[7] ..... A01H 5/00

(52) U.S. Cl. ..... Plt./257

(58) Field of Search ..... Plt./257

*Primary Examiner*—Kent Bell
*Assistant Examiner*—Louanne Krawczewicz Myers
(74) *Attorney, Agent, or Firm*—Christie, Parker & Hale, LLP

(57) ABSTRACT

A new plant variety of *Hibiscus rosa-sinensis* named 'Smiley Face', characterized by an intense red-orange bloom, spotted and splotched with yellow marks along the outer rime of the flower. It is a free-flowering plant with an upright, compact habit. The foliage is glossy and dark green.

4 Drawing Sheets

Botanical classification: *Hibiscus rosa-sinensis* L.
Varietal denomination: The new plant has the varietal denomination 'Smiley Face'.

BACKGROUND OF THE INVENTION

The present invention relates to a new and distinct variety of *Hibiscus rosa-sinensis* L., which was developed in a controlled breeding program in Webster, Tex.

The genus *Hibiscus* comprises about 250 species of herbs, shrubs and trees in warm temperate and tropical regions; with leaves usually simple, mostly palmately veined, lobed or parted; flowers mostly solitary in the leaf axils but sometimes in racemes, corymbs or panicles. *Hibiscus* is included in the family Malvaceae, which comprises about 95 genera of herbs, shrubs and trees originating in tropical and temperate regions. *Hibiscus rosa-sinensis* is a glabrate shrub, seldom over 8 feet tall in cultivation, but treelike to 15 feet or more in tropical regions. Leaves to 6-inches long, ovate, usually serrate, mostly glossy green. Flowers solitary in upper leaf axils.

The new *Hibiscus* is a product of a planned breeding program conducted by the inventor in Webster, Tex. The objective of the program was to create new *Hibiscus* selections with improved bloom quality, color and floriferousness, plants that can be commercially produced on their own root systems, and improved plant habit with regard to vigor and postproduction longevity.

SUMMARY OF THE INVENTION

The new variety was discovered in a controlled breeding program of *Hibiscus rosa-sinensis* and differs from its parents and other known cultivars of *Hibiscus rosa-sinensis* by the following characteristics in combination:

1. Upright, compact symmetrical plant habit that is suitable for container production;
2. Healthy green foliage;
3. Vigorous growth habit;

4. An intense red-orange bloom, spotted and splotched with yellow marks along the outer rim of the flower;
5. Free-flowering.

Asexual reproduction of the new variety by stem cuttings, performed in Webster, Tex. and Fulshear, Tex. have confirmed that the distinctive characteristics of the new variety are stable and transmitted to succeeding generations, and the new variety reproduces true to type.

COMPARISON WITH PARENTS AND OTHER CULTIVARS

'Smiley Face' is distinguished from its female parent 'Morgan Alyssa' (not patented) by having a different flower color combination: 'Morgan Alyssa' has dark red flowers with numerous white markings. Also, 'Morgan Alyssa' does not begin to bloom until it reaches a height of approximately 4 feet, while 'Smiley Face' will bloom in a #1 nursery container at a height of 12 inches. 'Smiley Face' is distinguished from its male parent 'Jazz' (not patented) by a lack of similarity in their flower colors and color patterns; flowers of 'Jazz' are orange with a metallic eye and a fuchsia halo, along with many yellow spots. Also, the flower color pattern of 'Jazz' is variable from bloom to bloom, while 'Smiley Face' has a bloom that is very consistent with its spotting and color. Also, the flowers of 'Smiley Face' have a heavier texture than those of 'Jazz'.

Plants of 'Smiley Face' can be compared to plants of the cultivar 'Golden Dust' (not patented). However, in side-by-side comparisons conducted in Webster, Tex., plants of 'Smiley Face' differ from plants of the cultivar 'Golden Dust' in the following characteristics:

1. Flowers of 'Smiley Face' are brighter in color than flowers of 'Golden Dust';
2. Plants of 'Smiley Face' are easier to propagate via vegetative cuttings than plants of the cultivar 'Golden Dust';
3. Plants of 'Smiley Face' possess healthier foliage and a better growth habit than the cultivar 'Golden Dust'.

BRIEF DESCRIPTION OF ILLUSTRATIONS

The accompanying illustrations show a plant of the new cultivar in a photographic illustration as true to color as is reasonably possible to make in an illustration of this character.

DETAILED DESCRIPTION OF THE NEW VARIETY

Figure 1:
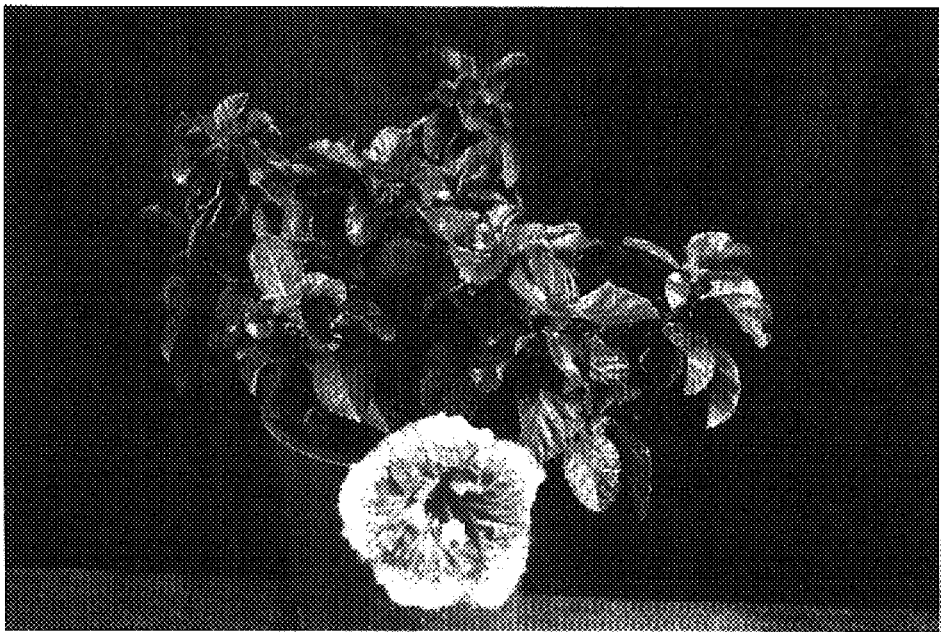
FIG. 1 illustrates a side perspective view of a typical plant of 'Smiley Face'.
Figure 2:
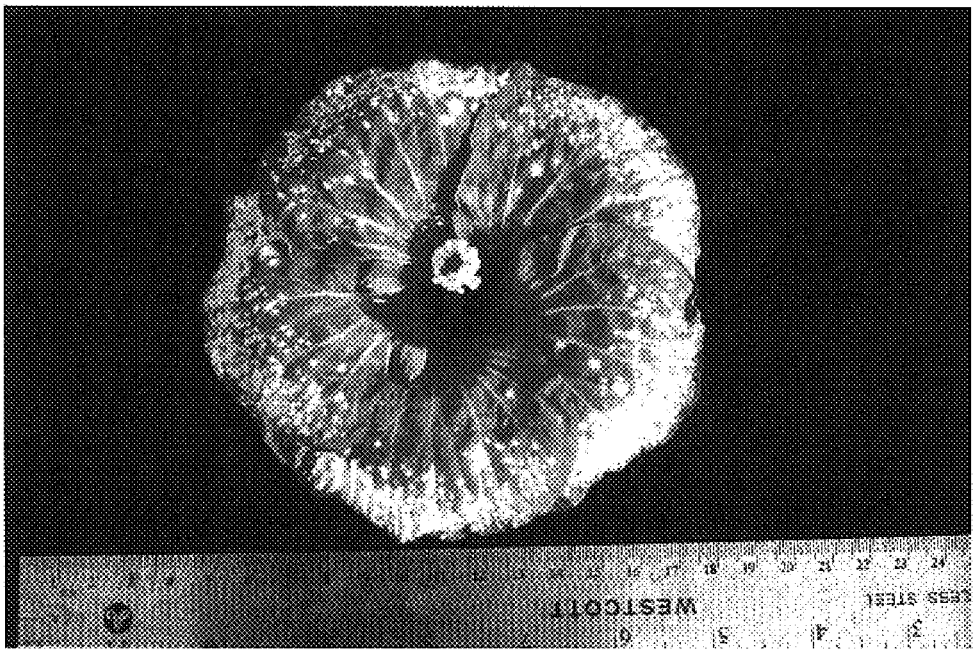
FIG. 2 illustrates the scale of a typical flower of 'Smiley Face'.
Figure 3:
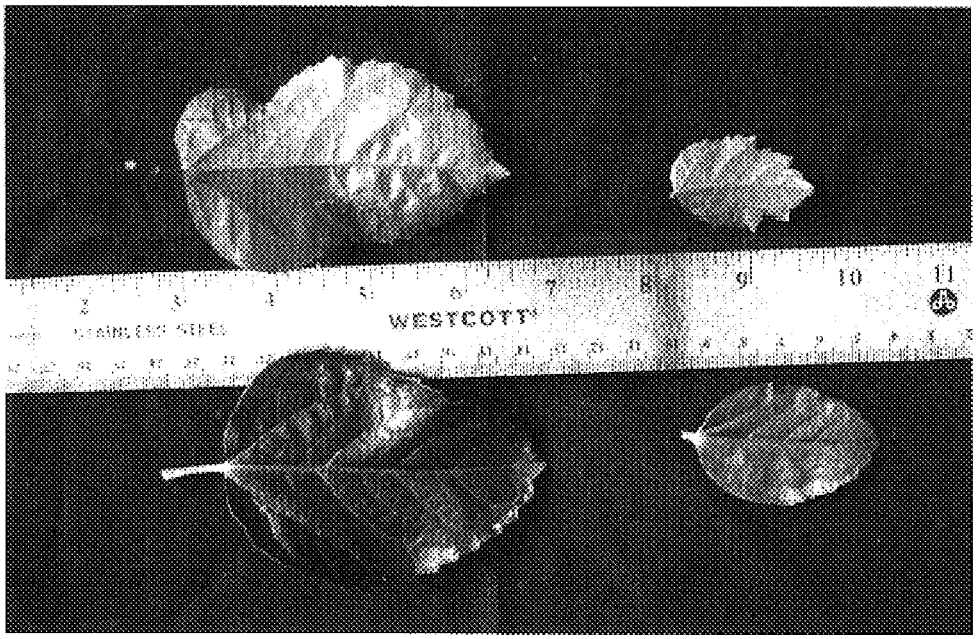
FIG. 3 illustrates the typical young to mature foliage of 'Smiley Face'; the abaxial and adaxial surfaces are shown at each stage.
Figure 4:
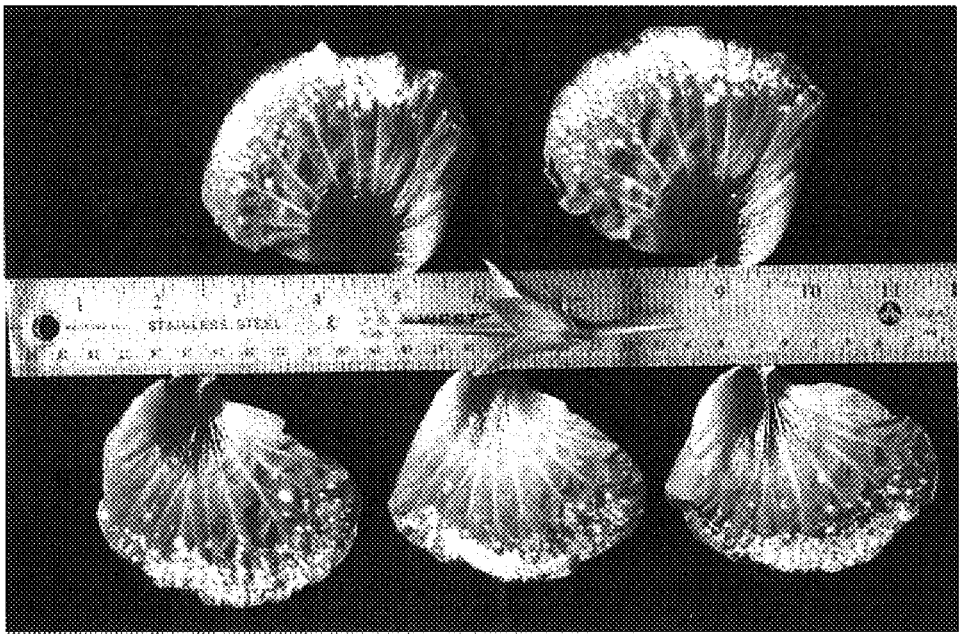
FIG. 4 illustrates a dissected flower of 'Smiley Face', including shape and size of petals and characteristics of the reproductive structures.

'Smiley Face' has not been observed under all possible environmental, cultural and light conditions. The following observations and descriptions are of plants grown in Fulshear, Tex., in November 2003, under polypropylene shadecloth providing a 30 percent light reduction, and under conditions which closely approximate commercial production. Plants described were approximately one year old and in a #3 nursery container. In this description, color references are to The Royal Horticultural Society Colour Chart (2000) and terminology used in the color descriptions herein refers to plate numbers in this color chart. Phenotypic expression may vary with light intensity, cultural and environmental conditions.

CLASSIFICATION

Botanical: *Hibiscus rosa-sinensis* L. 'Smiley Face'.
Parentage:
- *Female or seed parent.*—*Hibiscus rosa-sinensis* 'Morgan Alyssa' (not patented).
- *Male or pollen parent.*—*Hibiscus rosa-sinensis* 'Jazz' (not patented).

Propagation: By stem cuttings.
Time to initiate rooting: Approximately 14 to 21 days at 21–24 C.
Time to develop roots: Approximately 42 to 56 days at 21–24 C.
Root description: Fine to medium; fibrous; freely branching.

PLANT

Size:
- *Height.*—Approximately 51 cm from soil level to top of flowers.
- *Diameter/spread.*—Approximately 60 cm.

Form and growth habit: Perennial, evergreen shrub; mostly upright and somewhat spreading.
Branching: Freely branching; approximately 4 to 8 lateral branches develop after pinching.
- *Lateral branches.*—Approximately 15 cm long and 4 mm in diameter.
- *Internode length.*—Approximately 3 cm.

LEAF

Shape: Cordate.
- *Apex.*—Acute.
- *Base.*—Cordate.

Leaf size: Approximately 8.5 cm long and 6 cm wide.
Arrangement: Alternate, single; symmetrical.
Margin: Crenate.
Aspect: Undulate.
Texture/substance: Glabrous, shiny.
Coloration:
- *Young foliage.*—Upper side: Near Green Group 137B. Under side: Near Green Group 138B.
- *Mature foliage.*—Upper side: Near Yellow-Green Group 147A. Under side: Near Yellow-Green Group 147C.

Venation pattern: Palmate.
- *Venation color, upper surface.*—Near 147A.
- *Venation color, lower surface.*—Near 147C.

Petioles:
- *Size.*—Approximately 2.5 cm long, 3 mm across.
- *Coloration.*—Near Green Group 137A.
- *Texture.*—Smooth.

Hardiness: USDA Zone 10 (30° F. to 40° F.).
Pests/diseases: Resistance to known *Hibiscus* diseases had not been observed on plants grown under conditions approximating commercial practices.

INFLORESENCE

Bloom period: Typically year-round under subtropical and tropical conditions.
Flower arrangement: Arranged singly at terminal leaf axils; free-flowering with 3 to 4 flower buds and/or open flowers per terminal apex; flowers face upright and slightly outward.
Flower appearance: An intense red-orange bloom, spotted and splotched with yellow; flowers are open for about two days before closing; flowers persistent.
Flower diameter: Approximately 14 cm.
Buds (just prior to showing color):
- *Rate of opening.*—Approximately 1 or 2 days, depending on temperature.
- *Shape.*—Elliptic.
- *Length.*—Approximately 3 cm.
- *Diameter.*—Approximately 1.2 cm.
- *Color.*—Near Yellow-Green Group 144A.

Fragrance: None noted.
Petals:
- *Number/arrangement.*—Corolla consists of 5 overlapping petals.
- *Shape.*—Spatulate with rounded apex.
- *Size.*—Approximately 8 cm long and 8.5 cm wide.
- *Margin.*—Entire, but ruffled.
- *Texture.*—Smooth.
- *Color.*—Upper Surface: The "eye" or throat starts at near Red Group 46A and transitions to near Orange-Red Group N 30A to N 30C throughout the rest of the petal; spotting along the outer edge of the petals range from near Yellow-Orange Group 15B to 15C. Lower Surface: The majority is near Orange-Red Group N34B, eventually fading to near White Group 155B at the base of the petal; outer edges of petals are near Yellow-Orange Group 15D.

Sepals:
- *Number/arrangement.*—5 sepals fused into a star-shaped calyx.
- *Shape.*—Linear with acuminate apices.
- *Margin.*—Entire.
- *Color.*—Near Yellow-Green Group 144A.

Peduncles:

*Length.*—Approximately 4 cm.
*Diameter.*—Approximately 2 mm.
*Angle.*—Upright to about 45 degrees.
*Strength.*—Strong, flexible.
*Color.*—Near Yellow-Green Group 144A.

REPRODUCTIVE ORGANS

Androecium:

*Stamens.*—Numerous; approximately 50. Stamen Length: Approximately 5 mm. Filament Color: Near Red Group 48B.
*Anther size.*—Approximately 1 mm.
*Pollen amount.*—Abundant.
*Pollen color.*—Yellow-Orange Group 15A.

Gynoecium:

*Pistil length.*—Approximately 7 cm.
*Stigma appearance.*—5, rounded.
*Stigma diameter.*—Approximately 2 mm.
*Stigma color.*—Near Orange-Red Group 34A.
*Style color.*—Lower half near Red Group 47A; upper half near Red Group 47D.

Seed production: Seed production has not been observed.

I claim:

1. A new and distinct variety of *Hibiscus rosa-sinensis* plant, named 'Smiley Face', substantially as shown and described.

* * * * *